US00PP32780P2

(12) United States Plant Patent
Nyegaard

(10) Patent No.: US PP32,780 P2
(45) Date of Patent: Feb. 2, 2021

(54) MINIATURE ROSE PLANT NAMED 'POULPAH095'

(50) Latin Name: ***Rosa* hybrid**
Varietal Denomination: Poulpah095

(71) Applicant: Mogens Nyegaard, Fredensborg (DK)

(72) Inventor: Mogens Nyegaard, Fredensborg (DK)

(73) Assignee: POULSEN ROSER A/S, Fredensborg (DK)

( * ) Notice: Subject to any disclaimer, the term of this patent is extended or adjusted under 35 U.S.C. 154(b) by 0 days.

(21) Appl. No.: 16/602,253

(22) Filed: Sep. 4, 2019

(51) Int. Cl.
*A01H 5/02* (2018.01)
*A01H 6/74* (2018.01)

(52) U.S. Cl.
USPC ..... Plt./125

(58) Field of Classification Search
USPC ..... Plt./101, 123, 125
See application file for complete search history.

(56) References Cited

PUBLICATIONS

Poulsen Roser. 2020. (http://www.poulsenroser.com/assortment/rose-collections/patiohit/jasmine-hit.aspx) retrieved Jun. 2, 2020. 2 pages. (Year: 2020).*

* cited by examiner

*Primary Examiner* — Susan McCormick Ewoldt
*Assistant Examiner* — Karen M Redden

(57) ABSTRACT

A new garden rose plant of the miniature class which has abundant, yellow flowers and attractive foliage. This new and distinct variety has shown to be uniform and stable in the resulting generations from asexual propagation.

2 Drawing Sheets

Botanical designation: *Rosa* hybrid.
Variety denomination: 'Poulpah095'.

SUMMARY OF THE INVENTION

The present invention constitutes a new and distinct variety of rose plant which originated from a controlled crossing between the female seed parent, an unnamed seedling, and the male pollen parent, also an unnamed seedling. Both of the parent varieties are non-patented.

The two parents were crossed during the summer of 2011 and the resulting seeds were planted in a controlled environment in Fredensborg, Denmark. The new variety, named 'Poulpah095', originated as a single seedling from the stated cross.

The new variety may be distinguished from its male pollen parent and female seed parent primarily by the following characteristics. The male pollen parent plant grows to a height of 75 cm in one growing season, while the new variety 'Poulpah095' grows to a height of 50 cm. The female seed parent plant has light yellow flowers while the new variety has deep yellow flowers with other intonations of orange-red at the petal margins.

The objective of the hybridization of this rose variety was to create a new and distinct variety with unique qualities, such as:

1. Uniform and abundant yellow flowers;
2. Vigorous, but compact growth when propagated on its own roots;
3. Exceptional disease resistance; and
4. Early flowering.

This combination of qualities is not present in previously available commercial cultivars of this type, known to the inventor, and distinguish 'Poulpah095' from all other varieties of which we are aware.

As part of the rose development program, Mogens N. Olesen germinated the seeds from the aforementioned hybridization during winter of 2011 and conducted evaluations on the resulting seedlings in a controlled environment in Fredensborg, Denmark. 'Poulpah095' was selected in the spring of 2012 by the inventor as a single plant from the progeny of the aforementioned hybridization.

Asexual reproduction of 'Poulpah095' by rooted cuttings was first done by Mogens N. Olesen in the nursery in Fredensborg, Denmark in July, 2012. This initial and other subsequent asexual propagations conducted in controlled environments have demonstrated that the characteristics of 'Poulpah095' are true to type and are transmitted from one generation to the next.

DESCRIPTION OF THE DRAWING

The accompanying color illustrations show as true as is reasonably possible to obtain in color photographs of this type, the typical characteristics of the buds, flowers, leaves, and stems, of 'Poulpah095'.

Specifically illustrated in FIG. 1 of the drawings are open flowers, petals detached, sepals detached showing reproductive flower parts.

Figure 1:
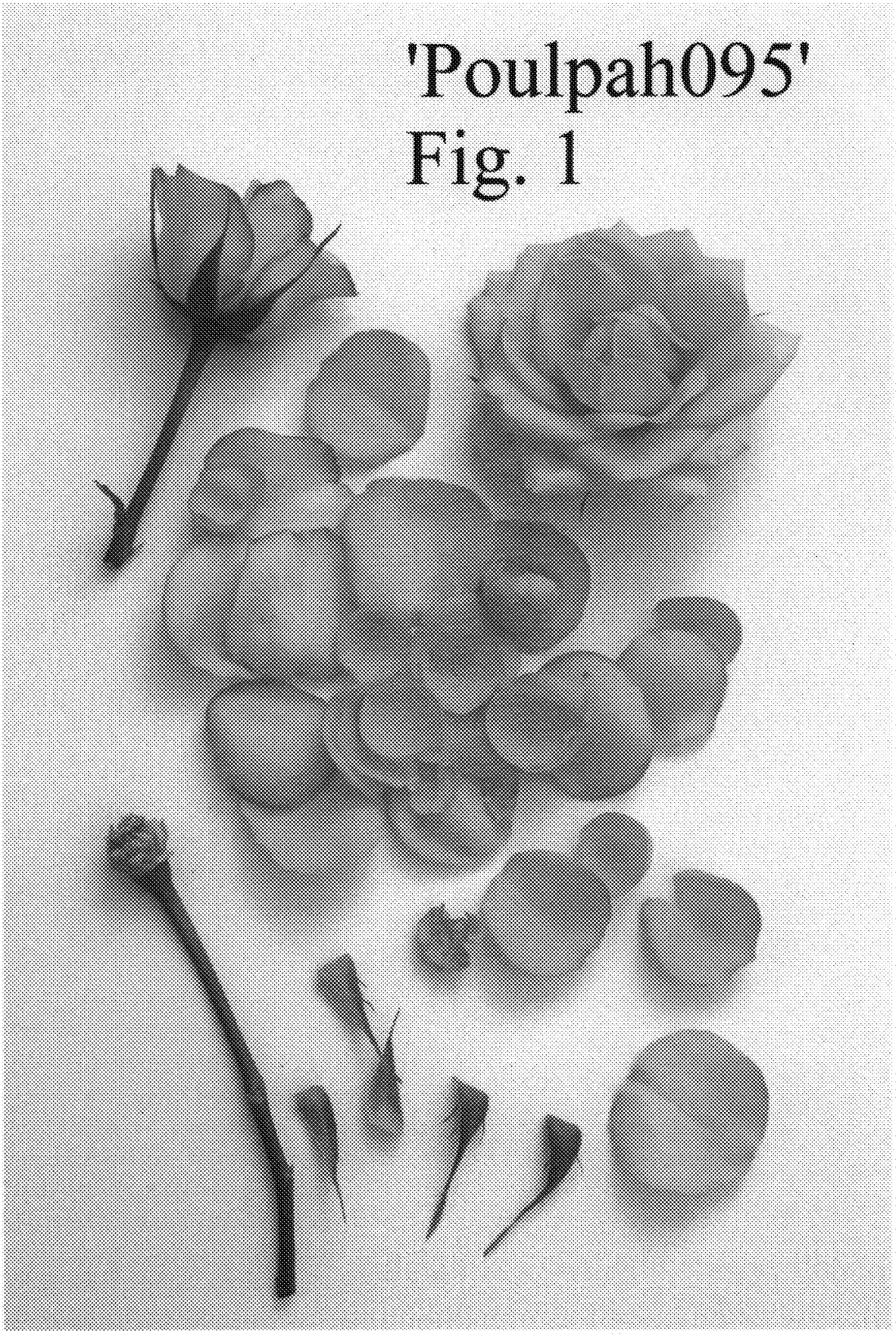
Figure 2:
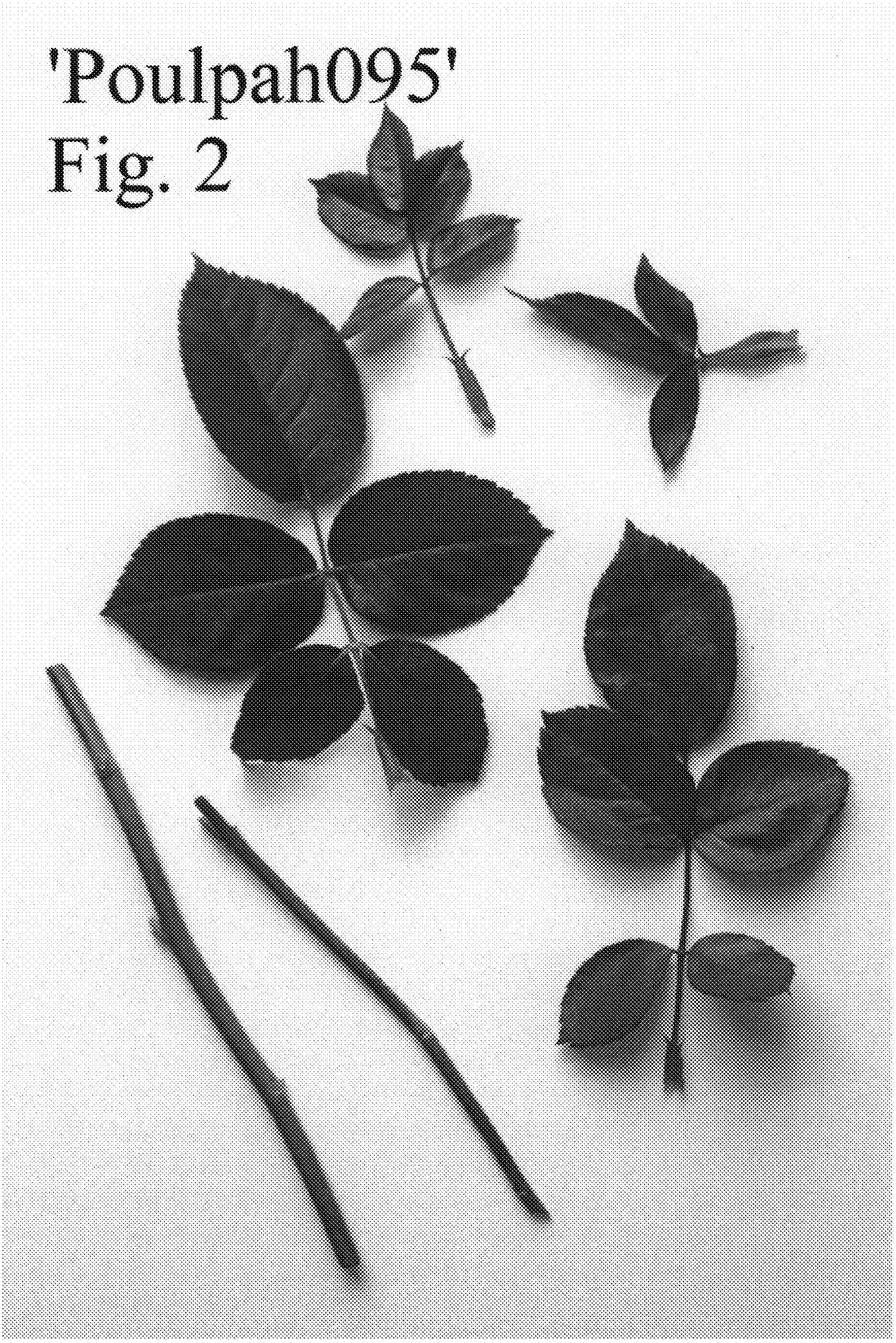

Specifically illustrated in FIG. 2 of the drawings are juvenile and mature stems and leaves. Plants shown are 2 years of age.

DETAILED DESCRIPTION OF THE VARIETY

The following is a description of 'Poulpah095', as observed in its growth in a glasshouse in Odense Denmark. Observed plants are 1 year old, and were grown on their own roots in 25 cm containers. Color references are made using The Royal Horticultural Society (London, England) Colour Chart, 2001, except where common terms of color are used.

For a comparison, several physical characteristics of the rose variety 'Poulpah064', U.S. Plant Pat. No. 25,971 are compared to 'Poulpah095' in Chart 1.

CHART 1

| | 'Poulpah095' | 'Poulpah064' |
|---|---|---|
| Petal Count | 36 petals | 60 petals |
| Flower Diameter | 75 mm | 35 mm |
| General Tonality of Flower Color | Yellow Group 12A | Yellow-Orange Group 14C with intonations of Yellow-Orange Group 22B |

FLOWER AND FLOWER BUD

Blooming habit: Continuous.

Flower bud:

*Size.*—Upon opening, 24 mm in length from base of receptacle to end of bud. Bud diameter is 15 mm.

*Bud form.*—Ovoid.

*Bud color.*—As sepals divide petals are Yellow-Green Group 1B.

*Sepal inner surface.*—Color: Yellow-Green Group 147C. Surface: Lightly pubescent.

*Sepal outer surface.*—Color: Yellow-Green Group 144A. Texture: Smooth.

*Sepal shape.*—Apex: Cirrhose. Base: Flat at union with receptacle.

*Sepal margin.*—Margins have weak foliaceous appendages on three of the five sepals.

*Sepal size.*—35 mm long, 8 mm wide.

*Receptacle.*—Texture: Smooth. Size: 5 mm in height, 7 mm wide. Color: Yellow-Green Group 144A. Shape: Funnel.

*Pedicel.*—Surface: Smooth. Length: About 45 mm. Diameter: 4 mm on average. Color: Yellow-Green Group 144B. Strength: Moderate.

Flower bud development: Flower buds are borne singly.

Flower bloom:

*Fragrance.*—Moderate floral scent.

*Duration.*—The blooms have a duration on the plant of approximately 15 days. Petals fall cleanly away from plant after flowers have fully matured.

*Size.*—Flower diameter is 75 mm when open. Flower depth is 30 mm.

*Flower shape.*—Rosette, double flower with many slightly overlapping petals of different sizes.

*Shape of flower, side view.*—The upper portion is a flattened convex. The lower portion is flat and concave.

Petalage: Under normal conditions, flowers have about 36 petals.

General tonality of flower: Open flowers are Yellow Group 12A.

Petal color:

*Upon opening, outer petals.*—Upper surface: Yellow Group 4B, at basal zone Yellow Group 12A. Lower surface: Yellow-Green Group 1C, and at the basal zone Yellow Group 12A. Margins are Greyed-Red Group 179B.

*Upon opening, inner petals.*—Upper surface: Yellow-Orange Group 17B. No distinctive color at the basal zone. Lower surface: Yellow Group 13A with margins the color of Orange-Red Group 33B. No distinctive color at the basal zone.

*After opening, outer and inner petals.*—Upper surface: Yellow 12B with distinct coloration of Yellow Group 12A at basal zone. Lower surface: Yellow-Green Group 1C, and at the basal zone Yellow Group 12A. Margins are Greyed-Red Group 179B.

Petals:

*Petal reflex.*—Moderate to strong.

*Margin.*—Entire and uniform.

*Shape.*—Broad and elliptic. Apex shape: Rounded. Base shape: Acute.

*Size.*—40 mm (l)×45 mm (w).

*Texture.*—Smooth.

*Thickness.*—Average.

Petaloids:

*Size.*—20 mm (l) by 14 mm (w).

*Quantity.*—About 5.

*Shape.*—Rounded. With both apex and base round in shape.

*Margins.*—Entire, with strong undulations.

*Color.*—Upper surface Yellow-Orange Group 17B. Lower surface is Yellow Group 13A with margins the color of Orange-Red Group 33B.

Reproductive flower parts:

*Pollen.*—None observed.

*Anthers.*—Size: 2 mm in length. Color: Yellow Group 11B. Quantity: 35 on average.

*Filaments.*—Color: Yellow Group 13B. Length: 4 mm.

*Pistils.*—Length: 10 mm. Quantity: 23 on average.

*Stigmas.*—Color: Greyed-Yellow Group 160B.

*Styles.*—Color: Greyed-Red Group 179B.

*Hips.*—None Observed.

PLANT

Plant growth: Upright. Plants are 50 cm in height, and 45 cm wide.

Stems:

*Color of juvenile growth.*—Yellow-Green Group 146C with intonations of Greyed-Orange Group 175A.

*Color of mature growth.*—Yellow-Green Group 146B.

*Length.*—Canes are about 25 cm from the base of the plant to the flowering portion.

*Diameter.*—About 4 mm.

*Internodes.*—On mature canes about 45 mm between nodes.

*Surface texture.*—Young wood: Smooth. Older wood: Smooth.

Long prickles: None observed.

Plant foliage:

*Compound leaf.*—155 mm (l)×120 (w).

*Quantity.*—2 or 3 leaves per 10 cm of stem on average.

*Leaf bearing angle to the stem.*—45 degrees.

*Color of juvenile foliage.*—Upper side: Yellow-Green Group 146B with intonations of Greyed-Purple Group 183A. Lower side: Yellow-Green Group 146B with intonations of Greyed-Orange Group 176B.

*Color of mature foliage.*—Upper side: Yellow-Green Group 147A. Lower side: Yellow-Green Group 147B.

Plant leaves and leaflets:

*Stipules*.—Size: 23 mm long, mm wide. Quantity: 2 per compound leaf Shape: Linear, slightly broad based with outward extending apices. Margins: Finely serrated. Color: Yellow-Green Group 144A.

*Petiole*.—Length: 33 mm. Diameter: 1.5 mm. Upper surface color: Yellow-Green Group 144A. Lower surface color: Yellow-Green Group 144B.

*Rachis*.—Length: 42 mm. Diameter: 1.5 mm. Upper surface color: Yellow-Green Group 144A. Lower surface color: Yellow-Green Group 144B.

*Leaflet*.—Quantity: Normally 5 leaflets. Margins: Serrated. Size: Terminal leaflets are about 70 mm long, 50 mm wide. Shape: Generally elliptical. Base: Rounded. Apex: Mucronate. Texture: Smooth. Thickness: Average. Arrangement: Odd pinnate. Venation: Reticulate. Glossiness: Moderately glossy.

Disease resistance: Above average resistance to powdery mildew *Sphaerotheca pannosa*, downy mildew *Peronospora sparsa*, rust *Phragmidium* sps., black spot *Diplocarpon rosae*, and *Botrytis cinerea* under normal growing conditions.

Cold hardiness: The variety is tolerant to USDA Cold Hardiness Zone 6.

Heat tolerance: The variety has been found to be suitable for climate conditions found in the American Horticulture Society heat zone 7.

I claim:

1. A new and distinct variety of rose plant of the miniature rose class named 'Poulpah095', substantially as illustrated and described herein, due to its abundant yellow flowers, disease resistance, and extended period of bloom.

* * * * *

'Poulpah095'

'Poulpah095'